(12) United States Patent
Russ et al.

(10) Patent No.: US 10,888,262 B2
(45) Date of Patent: Jan. 12, 2021

(54) VACUUM PRESSURE REGULATORS FOR USE DURING BLOOD COLLECTION

(71) Applicant: Becton, Dickinson and Company, Franklin Lakes, NJ (US)

(72) Inventors: Craig Owen Russ, Wayne, NJ (US); Neville Yu Leng Chia, Singapore (SG); Jamieson W. Crawford, Hagersten (SE); Kenneth James Smith, Flanders, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 226 days.

(21) Appl. No.: 14/889,211

(22) PCT Filed: May 15, 2013

(86) PCT No.: PCT/US2013/041181
§ 371 (c)(1),
(2) Date: Nov. 5, 2015

(87) PCT Pub. No.: WO2014/185905
PCT Pub. Date: Nov. 20, 2014

(65) Prior Publication Data
US 2016/0089070 A1  Mar. 31, 2016

(51) Int. Cl.
*A61B 5/15* (2006.01)
*G05D 7/01* (2006.01)
*A61B 5/154* (2006.01)
*A61M 5/168* (2006.01)
(Continued)

(52) U.S. Cl.
CPC ........ *A61B 5/150946* (2013.01); *A61B 5/153* (2013.01); *A61B 5/15003* (2013.01);
(Continued)

(58) Field of Classification Search
CPC .......... A61B 5/150946; A61B 5/15003; A61B 5/150221; A61B 5/150389;
(Continued)

(56) References Cited

U.S. PATENT DOCUMENTS 3,848,579 A  11/1974  Villa-Real
3,964,484 A  *  6/1976  Reynolds ............ A61M 1/3672
                                                    604/269
(Continued)

FOREIGN PATENT DOCUMENTS

CN           2538281 Y       3/2003
CN        101091654 A       12/2007
(Continued)

*Primary Examiner* — Daniel L Cerioni
(74) *Attorney, Agent, or Firm* — The Webb Law Firm

(57) ABSTRACT

A regulator for in-line modulation of the flow rate of fluid during blood collection includes a fluid transfer device for transferring fluid from a patient to a collection device. The fluid transfer device comprises a fluid passageway defined by a tubular sidewall and a flexible member associated with a portion of the tubular sidewall. The flexible member is configured for movement with respect to the fluid passageway upon exposure of the fluid transfer device to a differential pressure during a blood collection procedure to prevent collapse of a patients blood vessel. The flexible member of the regulator can be a frame surrounding a flexible diaphragm. Alternatively, the flexible member can include a flexible material integrally formed within the tubular sidewall of the pressure regulator.

12 Claims, 5 Drawing Sheets

(51) Int. Cl.
*A61B 5/153* (2006.01)
*A61M 39/24* (2006.01)

(52) U.S. Cl.
CPC .......... *A61B 5/154* (2013.01); *A61B 5/15074* (2013.01); *A61B 5/150221* (2013.01); *A61B 5/150389* (2013.01); *A61B 5/150503* (2013.01); *A61B 5/150572* (2013.01); *A61B 5/150587* (2013.01); *A61B 5/150717* (2013.01); *A61B 5/150992* (2013.01); *A61M 5/16813* (2013.01); *A61M 5/16881* (2013.01); *G05D 7/0113* (2013.01); *A61M 2039/246* (2013.01); *A61M 2039/2433* (2013.01)

(58) Field of Classification Search
CPC ........ A61B 5/150503; A61B 5/150572; A61B 5/150587; A61B 5/150717; A61B 5/15074; A61B 5/150992; A61B 5/153; A61B 5/154; A61M 5/16813; A61M 5/16881; G05D 7/0113
USPC .......................................................... 600/579
See application file for complete search history.

(56) References Cited

U.S. PATENT DOCUMENTS

| | | | |
|---|---|---|---|
| 4,154,229 A * | 5/1979 | Nugent | A61B 5/154 600/577 |
| 4,340,068 A | 7/1982 | Kaufman | |
| 5,284,473 A * | 2/1994 | Calabria | A61M 25/104 604/102.02 |
| 2004/0054348 A1* | 3/2004 | Hogendijk | A61M 5/16813 604/523 |
| 2005/0075612 A1 | 4/2005 | Lee et al. | |
| 2006/0009714 A1 | 1/2006 | Higaki et al. | |
| 2008/0066810 A1 | 3/2008 | Barak | |
| 2008/0086085 A1 | 4/2008 | Brown | |
| 2012/0180875 A1 | 7/2012 | Keller et al. | |
| 2013/0006148 A1 | 1/2013 | Matumura | |
| 2013/0197621 A1 | 8/2013 | Ryan et al. | |
| 2013/0303987 A1 | 11/2013 | Esnouf | |

FOREIGN PATENT DOCUMENTS

| | | |
|---|---|---|
| CN | 102802525 A | 11/2012 |
| EP | 0042211 A2 | 12/1981 |
| EP | 1614384 A2 | 1/2006 |
| EP | 1897585 A1 | 3/2008 |
| JP | 51110888 | 9/1976 |
| JP | 2006501888 A | 1/2006 |
| JP | 2007535985 A | 12/2007 |
| WO | 0037128 A1 | 6/2000 |
| WO | 0211613 A2 | 2/2002 |
| WO | 2004024210 A2 | 3/2004 |
| WO | 2012021406 A2 | 2/2012 |
| WO | 2012061869 A1 | 5/2012 |

* cited by examiner

VACUUM PRESSURE REGULATORS FOR USE DURING BLOOD COLLECTION

CROSS-REFERENCE TO RELATED APPLICATIONS

This application is the United States national phase of International Application No. PCT/US2013/041181 filed May 15, 2013 the disclosure of which is hereby incorporated in its entirety by reference.

BACKGROUND OF THE INVENTION

Field of the Invention

The present invention relates to a regulator for flow modulation to prevent the collapse of a patient's blood vessel during blood collection and, more particularly, to a variable flow resistor that acts to slow down the initial flow rate of blood into an evacuated blood collection device. The present invention also minimizes the initial spike in flow rate caused by vacuum pressure and slows down the overall blood collection time to avoid rapid depletion of resident blood within the vessel.

Description of Related Art

Phlebotomy procedures are often carried out using a blood collection device or intravenous (IV) infusion device. A typical blood collection or (IV) infusion device includes a needle assembly having a cannula that includes a proximal end, a pointed distal end, and a lumen extending therebetween. The needle assembly also includes a hub with a proximal end, a distal end, and a passage extending between the ends. The proximal end of the cannula is mounted in the passage of the hub so that the lumen of the cannula communicates with the passage through the hub. A shield may be provided for shielding the distal end of the cannula after use. The blood collection set may also include a wing member that projects transversely from the hub or from the shield. The wings of the wing member can be folded with respect to each other to define a handle that facilitates manipulation of the needle assembly. The wings then can be rotated apart and held against the skin of the patient.

Typical blood collection devices may also include a length of flexible plastic tubing. The tubing has a distal end that is connected to the proximal end of the hub and communicates with the lumen of the needle cannula. The end of the plastic tube remote from the needle cannula may include a fixture for connecting the needle cannula to a blood collection tube or other receptacle. Phlebotomy procedures often employ evacuated tubes, such as the VACUTAINER® brand of evacuated tubes commercially available from Becton, Dickinson and Company. Evacuated tubes often are used with a tube holder that has a proximal end, a distal end, and a tubular side wall extending between the ends. The proximal end of the holder is generally open and is configured for slidably receiving the evacuated tube. The distal end of the holder typically includes an end wall with a mounting aperture. The tube holder may be used with a non-patient needle assembly that has a non-patient hub configured for cooperation with the mounting aperture of the holder. The non-patient needle assembly further includes a non-patient cannula extending proximally from the hub and into the tube holder.

The blood collection set may be used by mounting the fitting at the proximal end of the flexible plastic tubing to the distal end of the hub of the non-patient needle assembly. The pointed distal end of the cannula is urged into a targeted blood vessel, such as a vein, by gripping the wings of the wing member for manipulation of the cannula. The wings may then be folded into engagement with the skin of the patient and may be taped in position. An evacuated tube is urged into the open proximal end of the blood collection tube holder so that the proximal end of the non-patient needle pierces the stopper of the evacuated tube. As a result, the blood vessel of the patient is placed in communication with the interior of the evacuated tube, and the pressure differential between the blood vessel and the evacuated tube will generate a flow of blood through the cannula, the hub, the flexible tubing, the non-patient hub, the non-patient needle, and into the evacuated tube.

Collapse of the patient's blood vessel during blood collection can occur as a result of a pressure differential created by the connection of the evacuated tube to the non-patient needle cannula. This collapse can occur as a result of the blood being removed too quickly from the patient's blood vessel due to the vacuum draw of the evacuated tube. When a standard evacuated tube is connected to a blood collection set, there is an instantaneous introduction of a sharp vacuum pressure applied to the patient's blood vessel. This strong vacuum results in a spiked flow rate of blood out of the patient's blood vessel. This sharp outflow of blood can lead to the vessel wall collapsing against the bevel of the distal end of the patient cannula, resulting in flow stoppage.

Accordingly, a need exists for a vacuum pressure regulator which minimizes the incidence of vessel or vein collapse.

SUMMARY OF THE INVENTION

The vacuum pressure regulator of the present invention minimizes vessel collapse by controlling the flow rate out of the patient's blood vessel. The present invention slows down the initial flow rate of blood into an evacuated tube to avoid the initial pressure spike.

In accordance with an embodiment of the present invention, a regulator for flow modulation during fluid collection to prevent the collapse of a patient's blood vessel includes a fluid transfer device for transferring fluid from a patient to a collection device. The fluid transfer device has a fluid passageway defined by a tubular sidewall and a flexible member associated with a portion of the tubular sidewall. Upon the exposure of the fluid transfer device to a differential pressure, the flexible member is configured for movement with respect to the fluid passageway to modulate a flow rate of the fluid. The flexible member forms a barrier between the fluid flowing through the fluid passageway and the atmosphere. The flexible member can comprise a spring element.

In certain configurations, the collection device can include an evacuated tube in fluid communication with the fluid passageway and wherein connection of the collection device to the evacuated tube creates a vacuum within the fluid passageway. Exposure of the fluid passageway to the vacuum creates a pressure gradient across the flexible member causing at least a portion of the flexible member to extend into the fluid passageway resulting in a restricted flow path within the fluid passageway.

According to one configuration, the flexible member can comprise a frame surrounding a flexible diaphragm. The tubular sidewall of the fluid transfer device can include an open portion and the frame surrounding the flexible diaphragm can be associated with the open portion such that the diaphragm is configured to extend through the open portion and into the fluid passageway upon exposure of the fluid transfer device to the differential pressure. According to another configuration, the flexible member can comprise a flexible material integrally formed within the tubular sidewall.

The flexible member can be configured to at least partially collapse toward the fluid passageway to restrict a flow area of the fluid passageway upon exposure of the fluid transfer device to the differential pressure. A venturi channel can be associated with the flexible member which can be adapted to accelerate the flow of fluid through an area adjacent the flexible member upon exposure to the differential pressure. The venturi channel is adapted to cause an increased pressure drop in a flow path adjacent thereto due to an increased pressure differential across the flexible member.

A thumb pad can be associated with the flexible member. This thumb pad can be adapted to enable a user to over-ride any automatic regulation of fluid flow and to manually regulate the flow of fluid through the fluid passageway.

In accordance with another embodiment of the present invention, a fluid transfer device including a regulator for flow modulation during blood collection includes a first cannula having a patient end, a second cannula having a non-patient end, a hub positioned between the first and second cannulae, and a tube holder associated with the second cannula. The tube holder can be configured for receiving a blood collection tube. The blood collection tube can include a seal for containing a vacuum therein which is adapted to be pierced by the second cannula to initiate the blood collection process. The regulator is associated with a fluid pathway of the fluid transfer device. The regulator includes a blood transfer device for transferring blood from a patient to a collection device. The blood transfer device comprises a blood flow passageway defined by a tubular sidewall and a flexible member is associated with a portion of the tubular sidewall. The flexible member is configured for movement with respect to the blood flow passageway upon exposure of the blood transfer device to a differential pressure. Application of the differential pressure within the blood flow passageway causes the automatic movement of the flexible member with respect to the blood flow passageway to modulate a flow of blood moving through the blood flow passageway. The application of the differential pressure is achieved by insertion of the blood collection tube within the tube holder and piercing of the seal of the blood collection tube.

In certain configurations, the flexible member can include a frame surrounding a flexible diaphragm. The tubular sidewall of the blood transfer device includes an open portion and the frame surrounding the flexible diaphragm is associated with the open portion such that the diaphragm is configured to extend through the open portion and into the blood flow passageway upon exposure of the blood transfer device to the differential pressure. In another configuration, the flexible member can comprise a flexible material integrally formed within the tubular sidewall. In both configurations, the flexible member is configured to at least partially collapse toward the blood flow passageway to restrict a flow area of the blood flow passageway upon exposure of the blood transfer device to the differential pressure.

A venturi channel can be associated with the flexible member which is adapted to accelerate the flow of fluid through an area adjacent the flexible member upon exposure to the differential pressure.

A thumb pad can be associated with the flexible member to enable a user to over-ride the automatic regulation of blood flow and to manually regulate the flow of blood through the blood flow passageway.

In accordance with another embodiment of the present invention, a method of regulating the flow of blood through a fluid transfer device during blood collection includes associating a vacuum pressure regulator with the fluid transfer device. The vacuum pressure regulator includes a blood transfer device for transferring blood from a patient to a collection device. The blood transfer device includes a blood flow passageway defined by a tubular sidewall, and a flexible member associated with a portion of the tubular sidewall. The method includes the steps of inserting a patient end of a cannula of the fluid transfer device into a patient and connecting a non-patient end of a cannula of the fluid transfer device with an evacuated blood collection container wherein the application of a vacuum pressure within a housing interior caused by the connection of the blood collection container causes the flexible member to automatically move with respect to the blood flow passageway to modulate the flow of blood moving through the blood flow passageway.

In certain configurations, the wingset includes a hub, tubing, and a blood collection holder, and the vacuum pressure regulator is positioned in-line with the tubing. A thumb pad can be associated with the flexible member to enable a user to over-ride the automatic regulation of blood flow and to manually regulate the flow of blood through the blood flow passageway.

According to one configuration, the flexible member can comprise a frame surrounding a flexible diaphragm. The tubular sidewall of the blood transfer device can include an open portion and the frame surrounding the flexible diaphragm can be associated with the open portion such that the diaphragm is configured to extend through the open portion and into the blood flow passageway upon exposure of the blood transfer device to the vacuum pressure. According to another configuration, the flexible member can include a flexible material integrally formed within the tubular sidewall. In both configurations, the flexible member is configured to at least partially collapse toward the blood flow passageway to restrict a flow area of the blood flow passageway upon exposure of the blood transfer device to the vacuum pressure.

The method can include associating a venturi channel with the flexible member. The venturi channel is adapted to accelerate the flow of fluid through an area adjacent the flexible member upon exposure to the vacuum pressure.

The method can also include associating a thumb pad with the flexible member to enable a user to over-ride the automatic regulation of blood flow and to manually regulate the flow of blood through the blood flow passageway.

In accordance with yet another embodiment of the present invention, a fluid transfer device includes a regulator for flow modulation during blood collection. The fluid transfer device includes a tube holder configured for receiving a blood collection tube, the blood collection tube including a seal for containing a vacuum therein. The tube holder defines a fluid pathway therein. The fluid transfer device includes a regulator associated with the fluid pathway. The regulator includes a blood flow passageway defined by a tubular sidewall, and a flexible member associated with a portion of the tubular sidewall. The flexible member is configured for movement with respect to the blood flow passageway upon exposure of the flexible member to a differential pressure. Application of the differential pressure within the blood flow passageway causes the automatic movement of the flexible member with respect to the blood flow passageway to modulate a flow of blood moving through the blood flow passageway.

In certain configurations, the application of the differential pressure is achieved by insertion of the blood collection tube within the tube holder and piercing of the seal of the blood collection tube. Optionally, the flexible member includes a frame surrounding a flexible diaphragm. The flexible member may include a flexible material integrally formed within the tubular sidewall. The flexible member may be configured to at least partially collapse toward the blood flow passageway to restrict a flow area of the blood flow passageway upon exposure of the blood transfer device to the vacuum pressure.

These and other features and characteristics of the present invention, as well as the methods of operation and functions of the related elements of structures, and the combination of parts and economies of manufacture, will become more apparent upon consideration of the following description with reference to the accompanying drawings, all of which form a part of this specification, wherein like reference numerals designate corresponding parts in the various figures.

DETAILED DESCRIPTION OF THE INVENTION

Figure 1:
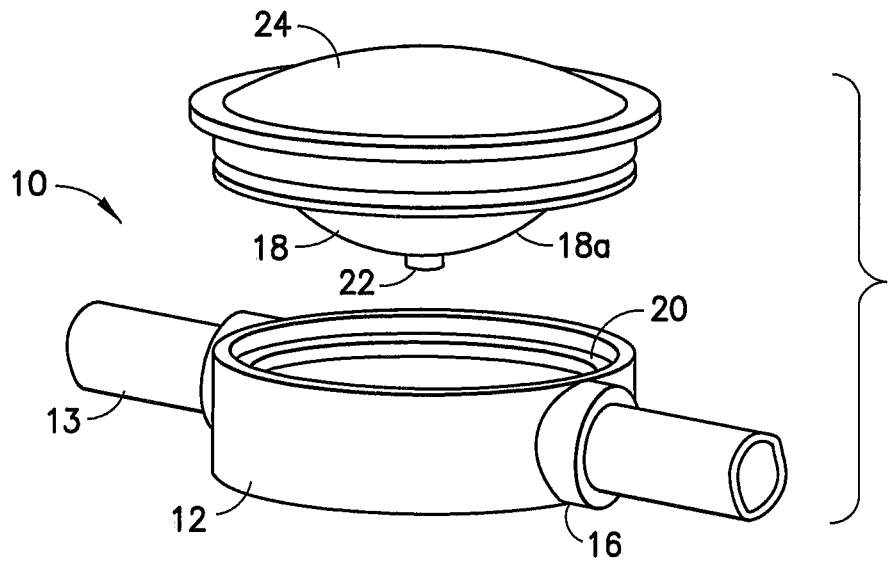
FIG. 1 is a front perspective view of a pressure regulator in accordance with an embodiment of the present invention.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1A:
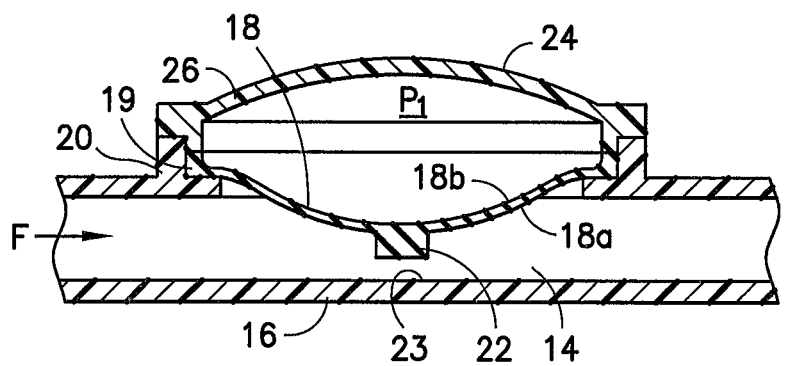
FIG. 1A is a cross-sectional side view of the pressure regulator of FIG. 1 having unrestricted flow of the fluid through the regulator in accordance with an embodiment of the present invention.
Figure 1B:
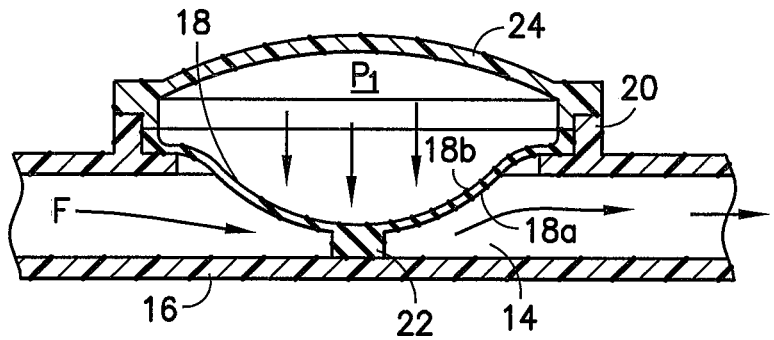
FIG. 1B is a cross-sectional side view of the pressure regulator of FIG. 1 showing a reduced pressure within the regulator resulting in a restricted flow of the fluid through the pressure regulator in accordance with an embodiment of the present invention.
Figure 3:
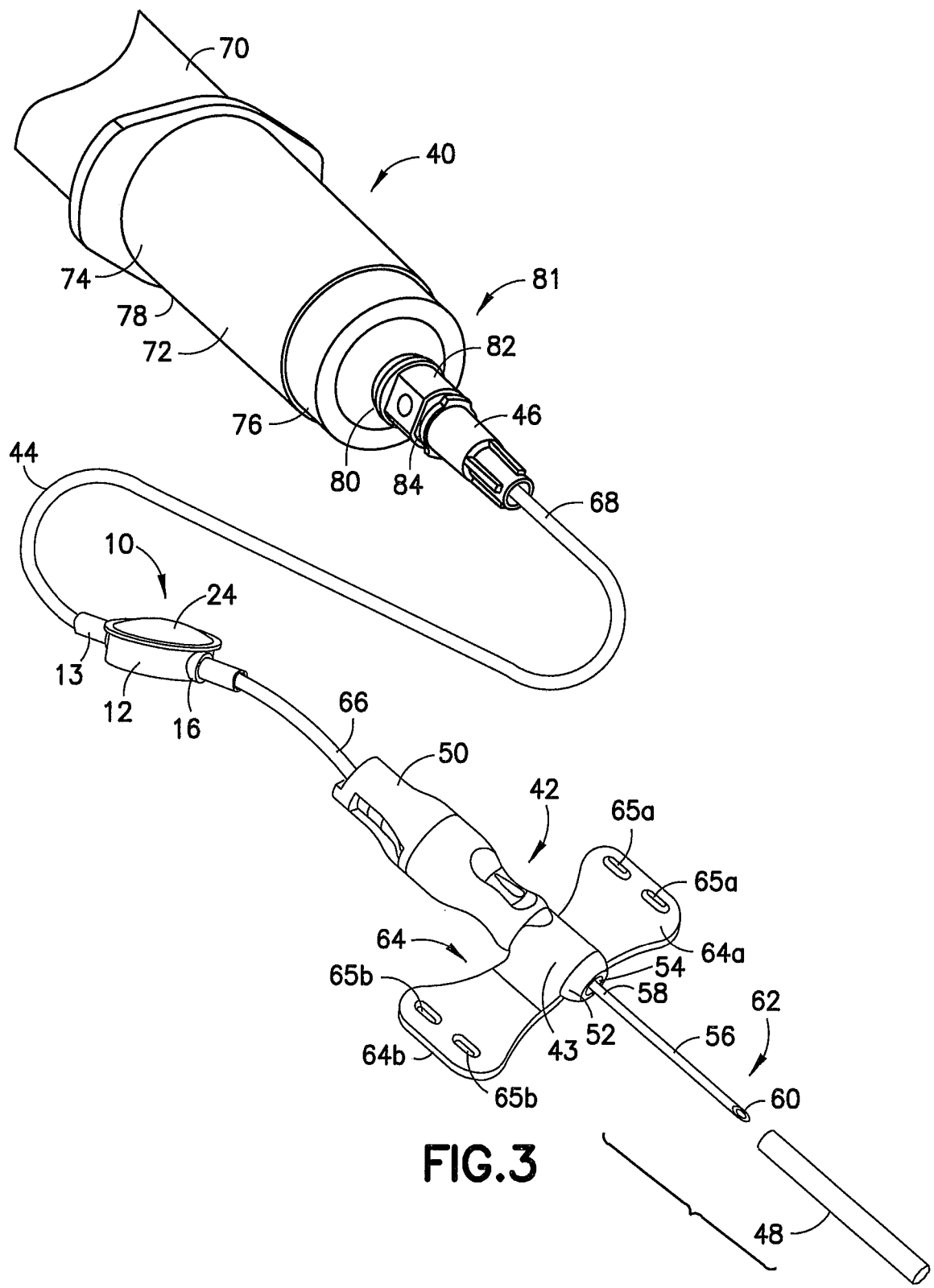
FIG. 3 is a front perspective view of an example of a fluid transfer device including the pressure regulator of FIG. 1 in accordance with an embodiment of the present invention.

Reference is now made to FIGS. 1, 1A, and 1B, which show a pressure regulator, generally indicated as 10, for flow modulation during fluid collection to prevent the collapse of a patient's blood vessel. The regulator 10 includes a fluid transfer device 12 for transferring fluid "F", such as in the form of blood from a patient to a collection device and/or for pulling a vacuum from the collection device to draw the blood. One type of collection device that can be used with the pressure regulator of the present invention, generally indicated as 40, is shown in FIG. 3 and described in detail below. Referring back to FIGS. 1, 1A, and 1B, the transfer of fluid "F" is achieved via a fluid transfer line 13. The fluid transfer device 12 has a fluid passageway 14 defined by a tubular sidewall 16 and a flexible member 18 having a periphery 19 that is associated with a portion 20 of the tubular sidewall 16 of the fluid transfer device 12. The flexible member 18 can be formed from any type of flexible, resilient material such as thermoplastic elastomers (TPE), silicone, and the like. Upon the exposure of the fluid transfer device 12 to a differential pressure, the flexible member 18 is configured for movement with respect to the fluid passageway 14 to modulate a flow rate of the fluid. The flexible member 18 has a first face 18a which is located adjacent to the fluid passageway 14 and a second face 18b which is located adjacent a first pressure $P_1$, such as atmospheric pressure or positive pressure. The flexible member 18 forms a barrier between the fluid "F" flowing in the fluid passageway 14 and the first pressure $P_1$. The flexible member 18 can exhibit spring type properties allowing it to return to its "at rest" or unrestricted position upon equalization of a vacuum pressure within the fluid passageway 14. Alternatively, a separate spring element can be provided allowing the flexible member 18 to return to its original position upon an equalization of pressure within the fluid passageway 14. It can be appreciated that a separate spring member (not shown) can be incorporated adjacent to the second face 18b of the flexible member 18. A cover 24 may be provided to protect the fluid transfer device 12 from dirt, debris, and/or to prevent inadvertent damage or actuation of the flexible member 18. Additionally, cover 24 can be modified to act as a thumb pad 26 which can be adapted to enable a user to over-ride any automatic regulation of fluid flow "F" and to manually regulate the flow of fluid through the fluid passageway 14.

Reference is now made to FIG. 3 which shows an example of one type of fluid collection device or blood collection device, generally indicated as 40, with which the pressure regulator 10 can be used. The pressure regulator 10 can be positioned in a variety of locations, as discussed in detail below, along the blood collection device 40 to regulate the flow rate of a patient's blood and minimize the occurrence of vessel/vein collapse. The blood collection device 40 can be in the form of a wingset and include a needle device, generally indicated as 42, including a hub 43, which can include a shielding device (not shown), a flexible tube 44 extending from the needle device 42, and a fixture 46 mounted to the tube 44. An optional packaging cover 48 can be removably mounted to the needle device 42 opposite tube 44, such as through frictional engagement or any other well known mounting arrangement. The hub 43 includes a proximal end 50, a distal end 52, and a passage 54 extending between the ends. A needle cannula 56 is provided which includes a first or proximal end 58 and an opposing second or distal end 60 and a lumen 62 extending through the cannula 56. The proximal end 58 of the cannula 56 is mounted in the passage 54 of the hub 43 so that the lumen 62 through the cannula 56 communicates with the passage 54 through the hub 43.

The blood collection device 40 may also include a wing member, generally indicated as 64, that projects transversely from the hub 43 or from the shield (not shown). The wing member 64 can include a pair of wings 64a, 64b that can be folded with respect to each other and secured together, such as with male and female interlocking members 65a, 65b, to define a handle that facilitates manipulation of the needle device/hub 42, 43. Once the needle device 42 is in position, such as once the needle cannula 56 has been inserted into the patient's vein or artery, the wings 64a, 64b can be unlocked and rotated away from one another and held or secured, such as by surgical tape, against the skin of the patient. As discussed above, the blood collection device 40 also includes a length of flexible plastic tubing 44. The tubing 44 has a distal end 66 that is connected to the proximal end 50 of the hub 43 and communicates with the lumen 62 of the needle cannula 56. A proximal end 68 of the tubing 44 may include a fixture 46 for connecting the needle cannula 56 to a blood collection tube or other receptacle 70. A holder 72 may be provided to hold the tube or other receptacle 70. The specific construction of the fixture 46 will depend upon the characteristics of the receptacle 70 to which the fixture 46 is to be connected.

Figure 5:
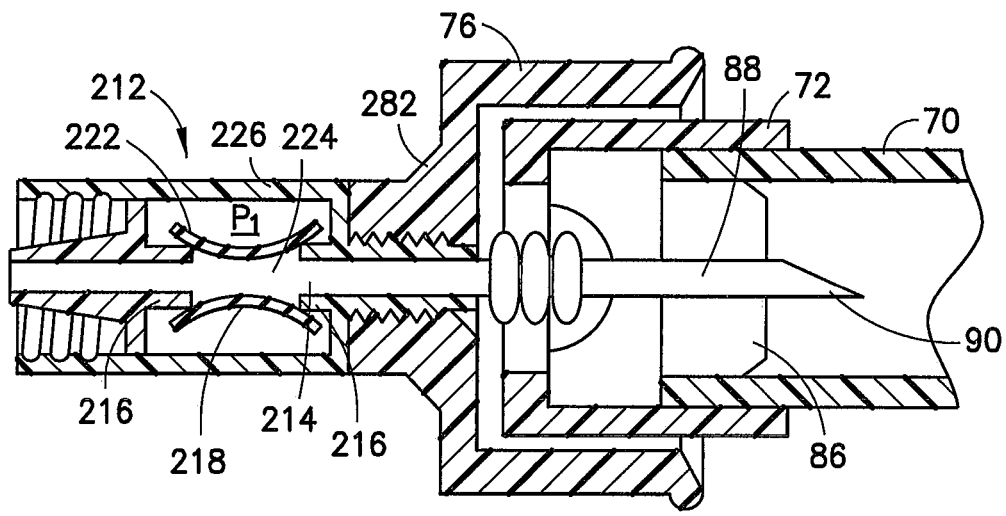
FIG. 5 is a cross-sectional side view of the pressure regulator of FIG. 4 in accordance with an embodiment of the present invention.

With continuing reference to FIG. 3 and with reference to FIG. 5, one type of receptacle 70 that is often used with blood collection devices is an evacuated tube. Evacuated tubes 70 often are used with a tube holder 72 that has a proximal end 74, a distal end 76, and a tubular side wall 78 extending between the ends 74, 76. The proximal end 74 of the holder 72 is widely open and is configured for slidably receiving the evacuated tube 70. The distal end 76 of the holder 72 typically includes an end wall with a mounting aperture 80. The tube holder 72 may be used with a non-patient needle assembly, generally indicated as 81, that has a non-patient hub 82 configured for cooperation with the mounting aperture 80 of the holder 72. The non-patient needle assembly 81 further includes a non-patient cannula, shown as 88 in FIG. 5, extending proximally from the hub 82 and into the tube holder 72.

The blood collection device 40 may be used by mounting the fixture 46 at the proximal end 68 of the flexible plastic tubing 44 to a distal end 84 of the hub 82 of the non-patient needle assembly 81. The pointed distal end 60 of the cannula 56 is urged into a targeted blood vessel, such as a vein, by gripping of the wings 64a, 64b of the wing member 64 for manipulation of the cannula 56. The wings 64a, 64b may then be folded into engagement with the skin of the patient and may be taped in position. With further reference to FIG. 5, an evacuated tube 70 is urged into the open proximal end 74 of the blood collection tube holder 72 so that a proximal end 90 of the non-patient cannula 88 pierces a stopper 86 of the evacuated tube 70. As a result, the blood vessel of the patient is placed in communication with the interior of the evacuated tube 70, and the pressure differential between the blood vessel and the evacuated tube 70 will generate a flow of blood through the cannula 56, the passage 54 of the hub 43, the flexible tubing 44, the non-patient hub 82, the non-patient cannula 88, and into the evacuated tube 70.

Collapse of the patient's blood vessel during blood collection can occur as a result of the pressure differential created by the connection of the evacuated tube 70 to the non-patient needle cannula 88. This collapse can occur as a result of the blood being removed too quickly from the patient's vessel. Physiological conditions such as the elasticity of the vessel wall can also contribute to this problem. With a standard evacuated tube 70, there is an instantaneous introduction of a sharp vacuum pressure when the evacuated tube 70 is attached to the non-patient end of the blood collection device 40. This strong vacuum results in an initially high flow rate of blood out of the patient's blood vessel. This sharp outflow of blood coupled with the high elasticity of a patient's vessel can lead to the vessel wall being pulled down onto the bevel of the distal end 60 of the patient cannula 56 resulting in flow stoppage.

With continuing reference to FIG. 1 and FIGS. 1A and 1B, the pressure regulator 10 of the present invention is associated with the blood collection device 40 to modulate the flow of fluid, i.e., both the flow of vacuum pressure and the flow of blood, during blood collection to prevent the collapse of a patient's blood vessel. Specifically, the pressure regulator 10 controls the level of vacuum pull or vacuum pressure moving through the blood collection device 40 so as to minimize the effect of the initial sharp pull of vacuum caused by the connection of the vacuum tube 70 to the non-patient cannula 88 and to slow down the removal of the blood from the patient's blood vessel. This control of fluid flow prevents or minimizes collapse of the patient's blood vessel. The pressure regulator 10 can be placed in-line with the flexible tube 44 of the blood collection device 40 resulting in a linear flow through architecture. The flexible member 18 can serve two functions. This first function of the flexible member 18 is to provide spring-like characteristics for restricting the fluid flow "F" based upon the level of vacuum pull and/or the result of atmospheric pressure applied to the second face 18b. The second function of the flexible member 18 is to act as a barrier between the blood and the outside air. A contact member 22 may be provided on the first face 18a of the flexible member 18. This contact member 22 can form a contact point between the flexible member 18 and an inner surface 23 of the fluid passageway 14 to form a sealing point therewith to stop the fluid flow F through the passageway 14. This contact member 22 can be a separate member joined to the flexible member 18 or it may be integrally formed with and from the same material as the flexible member 18.

In operation, a method of regulating the flow of blood through a blood collection device 40 during blood collection includes associating the pressure regulator 10, as discussed above, with the blood collection device 40. The method includes the steps of inserting a patient or distal end 60 of the cannula 56 of the blood collection device 40 into a patient and connecting a non-patient end of a cannula 88, as shown in FIG. 5, of the blood collection device 40 with an evacuated tube 70 wherein the application of a vacuum pressure within the housing interior caused by the connection of the evacuated tube 70 causes the flexible member 18 to automatically move with respect to the passageway 14 to modulate the flow of blood moving through the blood flow passageway 14. As shown in FIG. 1B, during the initial spike of vacuum pressure within the pressure regulator 10 and the fluid transfer device 12, the flexible member 18 can be drawn down into the fluid transfer line 13 until the contact member 22 abuts the inside surface 23 of the fluid passageway 14.

Reference is now made to FIGS. 2 and 2A-2C which show a pressure regulator, generally indicated as 110, in accordance with an embodiment of the present invention for flow modulation during fluid collection to prevent the collapse of a patient's blood vessel. This pressure regulator 110 is similar in design to the pressure regulator 10 shown in FIGS. 1 and 1A-1B, but does not include the cover member 24. The pressure regulator 110 includes a venturi channel 130, as discussed below. The regulator 110 further includes a fluid transfer device 112 for transferring fluid "F", from a patient to a blood collection tube within a collection device 40, as shown in FIG. 3, via a fluid transfer line 113. The fluid transfer device 112 has a fluid passageway 114 defined by a tubular sidewall 116 and a flexible member 118 having a periphery 119 that is associated with an open frame 120 of the fluid transfer device 112. The flexible member 118 can be secured to the frame 120 by any known type of clamping arrangement.

Figure 2:
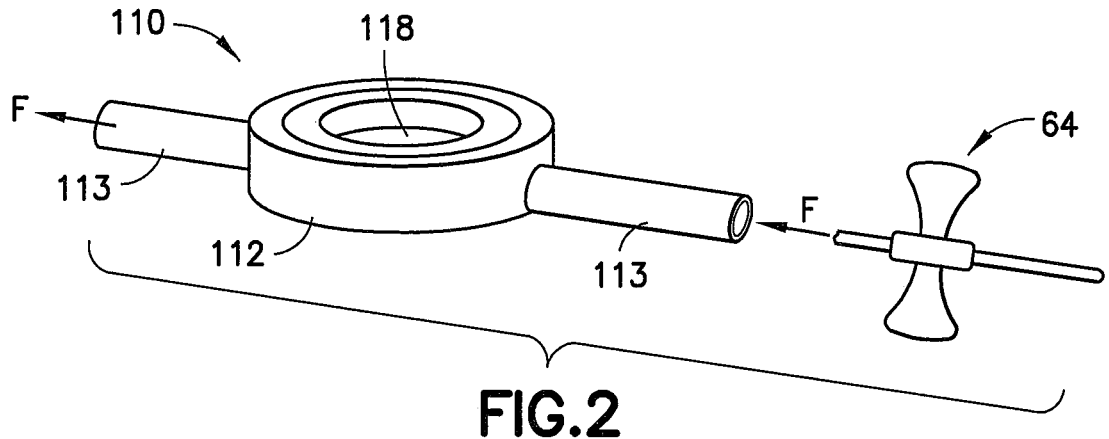
FIG. 2 is a front perspective view of a pressure regulator in accordance with an embodiment of the present invention.
Figure 2A:
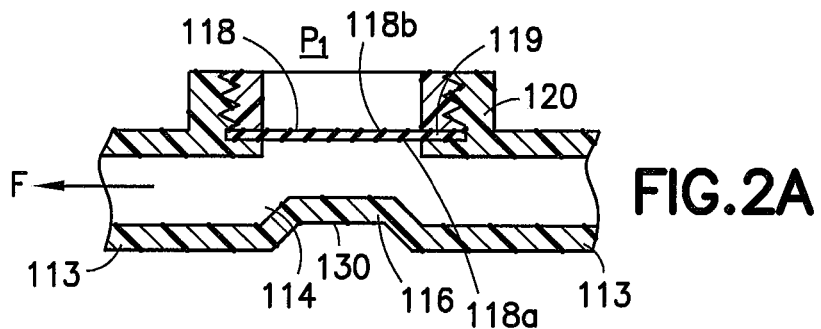
FIG. 2A is a cross-sectional side view of the pressure regulator of FIG. 2 showing unrestricted flow of the fluid through the regulator in accordance with an embodiment of the present invention.
Figure 2B:
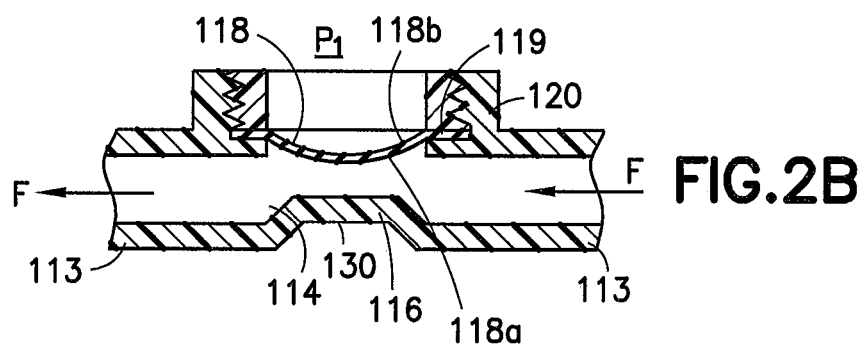
FIG. 2B is a cross-sectional side view of the pressure regulator of FIG. 2 showing a reduced pressure within the regulator resulting from the initial attachment of a collection tube resulting in a restricted flow of the fluid through the pressure regulator in accordance with an embodiment of the present invention.
Figure 2C:
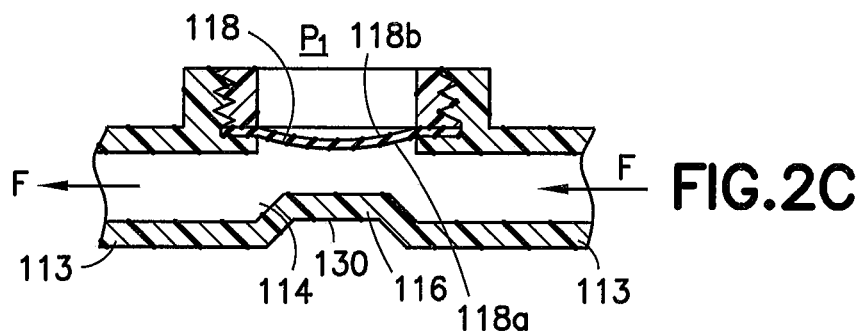
FIG. 2C is a cross-sectional side view of the pressure regulator of FIG. 2 showing a partially restricted flow of the fluid through the regulator in accordance with an embodiment of the present invention.

Referring to FIG. 2A, there is shown the pressure regulator 110 showing unrestricted flow of fluid, i.e., blood through the pressure regulator 110 and along fluid transfer line 113 from a wing member 64 of a blood collection device 40 to a blood collection or vacuum tube as is known in the art. The flexible member 118 has a first face 118a which is located adjacent to the fluid passageway 114 and a second face 118b which is located adjacent the first pressure $P_1$. The flexible member 118 forms a barrier between the fluid "F" flowing in the fluid passageway 114 and the first pressure $P_1$. Referring now to FIG. 2B, there is shown the pressure regulator 110 upon the connection of a blood collection tube, such as a blood collection tube 70, as previously described, to the blood collection device, such as the collection device 40 shown in FIG. 3, causing an initial spike of vacuum pressure within the fluid transfer line 113 and the flexible tube 44 of the blood collection device 40. This initial spike of vacuum pressure cooperates with first pressure $P_1$, such as atmospheric or positive pressure, to draw the flexible member 118 into the fluid transfer line 113 of the fluid transfer device 112 to modulate or restrict the amount of vacuum pressure applied to the patient's blood vessel and to restrict the flow rate of blood moving through the pressure regulator 110. Referring now to FIG. 2C, as the blood collection tube 70 begins to fill with blood, the vacuum pressure within the fluid transfer device 112 begins to equalize with first pressure $P_1$, causing the flexible member 118 to move out of the fluid passageway 114 forming a larger area for flow of the fluid therethrough.

As discussed above, the flexible member 118 can be formed from a flexible and/or elastomeric member that can exhibit spring type properties or a separate spring element (not shown) can be provided adjacent the second face 118b of the flexible member 118 which cooperates with the flexible member 118 to cause the flexible member 118 to return to its original position upon an equalization of pressure within the fluid passageway 114. The pressure regulator 110 can be embodied with a venturi type channel 130 which cooperates with the flexible member 118 to accelerate the flow of fluid through the area defined by the channel 130 and the flexible member 118. This type of arrangement would cause an increased pressure drop in the fluid path through the fluid passageway 114 and result in an increased pressure differential across the flexible member 118. It can be appreciated that a thumb pad (not shown) could be provided to allow a user to over-ride the automatic regulation of the flow rate and manually slow down the flow of blood flowing through the fluid transfer device 112.

Figure 4:
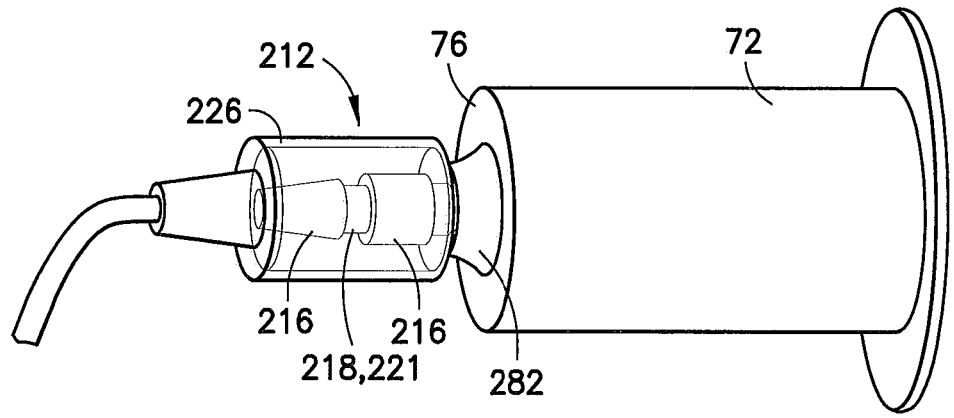
FIG. 4 is a side perspective view of a pressure regulator in accordance with another embodiment of the present invention.

Reference is now made to FIGS. 4 and 5 which show a pressure regulator, generally indicated as 212, in accordance with another embodiment of the present invention in connection with a fluid transfer device. In this embodiment, a flexible member 218 can comprise a flexible material 221 integrally formed within or secured to a tubular sidewall 216 defining a fluid passageway 214. This design also allows for a linear flow through architecture. It can be appreciated that although FIGS. 4 and 5 show the device located within a non-patient hub 282 adjacent a holder 72 for a blood collection tube 70, it can be appreciated that the pressure regulator could be located at any location in-line with a blood collection device adjacent the proximal end 50 of the patient hub 43 or at any location in-line with the flexible tube 44.

Figure 5A:
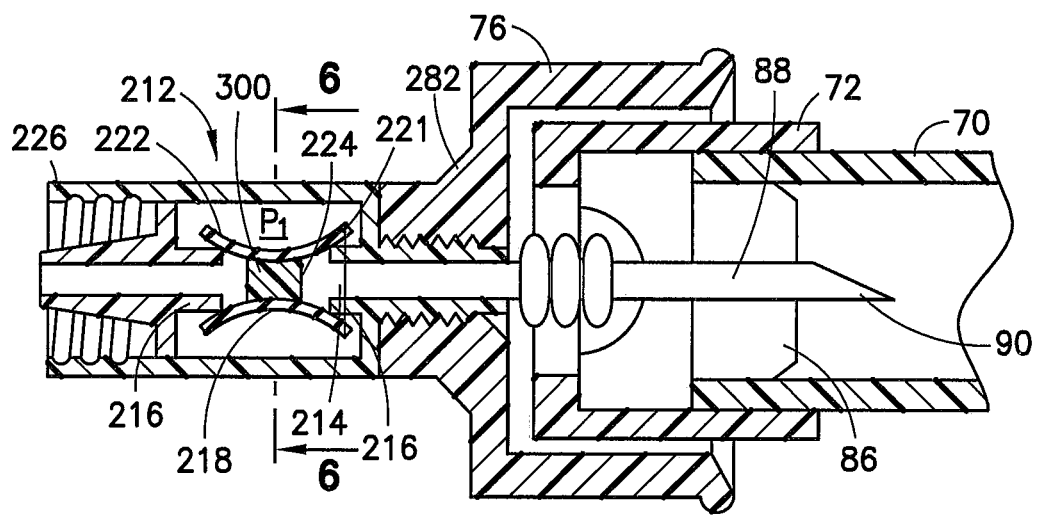
FIG. 5A is a cross-sectional side view of a pressure regulator having a ridge disposed adjacent the flexible member in accordance with an embodiment of the present invention.
Figure 6:
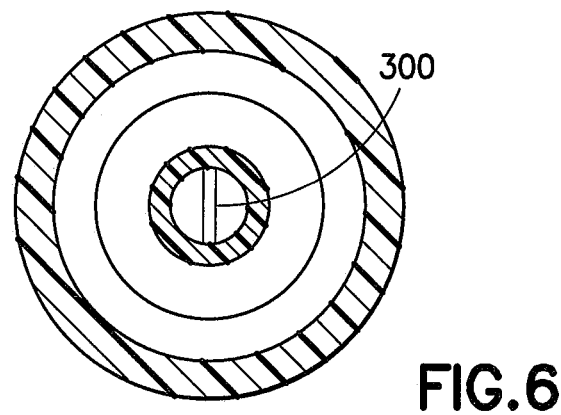
FIG. 6 is a cross-sectional view of the pressure regulator of FIG. 5A taken along line 6-6 in accordance with an embodiment of the present invention.

With continuing reference to FIGS. 4 and 5, the pressure regulator 212 also relies upon a pressure gradient acting across the flexible member 218 to restrict the flow of fluid "F" through the pressure regulator 212, as shown in FIGS. 2-2C. As stated above, the flexible member 218 is formed from a flexible material 221. This flexible material 221 can form a tube 222 defining a variable flow path 224 wherein the tube 222 acts as a barrier between blood, flowing along the flow path 224 inside the tube 222, and first pressure $P_1$ located outside of the tube. Upon the insertion of the blood collection tube 70 into the holder 72 and piercing of the stopper 86 by the proximal end 90 of the non-patient cannula 88, an initial spike in vacuum pressure communicated to the pressure regulator 212 causes the material 221 of the tube 222 to collapse an amount sufficient to restrict the flow of fluid without collapsing on itself and completely shutting of the flow of fluid. In particular, the material 221 forming tube 222 can be engineered to collapse a predetermined amount based on an anticipated amount of vacuum pressure by specifying the appropriate thickness, diameter, and material properties (elasticity, etc.) so as to avoid completely collapsing in on itself and cutting off the flow of fluid. Alternatively, or in addition to engineering the material 221 of the tube 222 to control the level of collapse, the tube 222, as shown in FIG. 5A, could be designed with an internal ridge 300, shown in FIGS. 5A and 6, which would allow some flow to continue to pass through after the larger tubing 222 has collapsed. A protective cover 226 can be positioned about the tube 222 to protect the tube 222 and prevent any debris from entering into the pressure regulator 212.

In operation, during the initial spike in vacuum pressure, the tube 222 collapses to create a restricted flow path, however, as the fluid pressure rises within the tube 222 upon the filling of the collection tube 70 with blood, the flexible tube 222 slowly returns to its original shape allowing for unrestricted flow of blood through the pressure regulator 212. The end result is high flow resistance early in the collection process when the vacuum pressure from the evacuated collection tube 70 is at its greatest and the risk of vein or vessel collapse is also at its greatest.

The pressure regulator 212 can be modified into a semi-automated device by connecting the flexible member 218 to a thumb pad (not shown) to over-ride the automatic regulation and to manually slow down the flow of blood moving through the pressure regulator 212.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

The invention claimed is:

1. A regulator for flow modulation during fluid collection, comprising:
a fluid transfer device comprising a tubular sidewall and a flexible member, wherein the flexible member is integrally formed within or secured to the tubular sidewall, wherein the tubular sidewall and the flexible member define a fluid passageway, wherein the flexible member comprises a first face that faces an inner surface of the fluid passageway, wherein the tubular sidewall defines the inner surface of the fluid passageway directly opposite the first face of the flexible member, wherein the flexible member comprises a second face opposite the first face, wherein the second face is located outside the fluid passageway, and wherein the first face and the second face are configured for movement with respect to the fluid passageway upon exposure of the fluid transfer device to a differential pressure resulting in the fluid passageway having a linear flow through architecture, wherein the flexible member is configured to at least partially collapse toward the inner surface of the fluid passageway to restrict a flow area of the fluid passageway upon exposure of the fluid transfer device to the differential pressure, wherein a contact member is provided on the first face of the flexible member, wherein the contact member extends from the first face of the flexible member toward the inner surface of the fluid passageway directly opposite the first face of the flexible member, and wherein, during an initial spike of vacuum pressure when the fluid transfer device is exposed to the differential pressure, the contact member abuts the inner surface of the fluid passageway to form a sealing point therewith to stop fluid flow through the fluid passageway.

2. The regulator of claim 1, wherein the flexible member comprises a spring element incorporated adjacent to the second face.

3. The regulator of claim 1, wherein the flexible member includes a periphery surrounding the first face and the second face, and wherein the periphery is integrally formed within or secured to the tubular sidewall.

4. The regulator of claim 3, wherein a portion of the flexible member completely surrounded by the periphery and including the first face and the second face is configured for movement with respect to the fluid passageway upon exposure of the fluid transfer device to the differential pressure.

5. The regulator of claim 1, wherein the fluid transfer device comprises a circular fluid transfer device, wherein the flexible member comprises a circular flexible member including a flexible diaphragm and a frame, wherein the frame surrounds the flexible diaphragm, and wherein an entire circumference of the circular flexible member is secured to the frame by a clamping arrangement.

6. The regulator of claim 5, wherein the tubular sidewall of the fluid transfer device includes an open portion, and wherein the frame surrounding the flexible diaphragm is associated with the open portion such that a portion of the flexible diaphragm including the first face and the second face is configured to extend toward the inner surface of the fluid passageway upon exposure of the fluid transfer device to the differential pressure.

7. The regulator of claim 4, wherein the portion of the flexible member surrounded by the periphery and including the first face and the second face is configured to at least partially collapse toward the inner surface of the fluid passageway to restrict the flow area of the fluid passageway upon exposure of the fluid transfer device to the differential pressure, and wherein the first face is permanently located directly adjacent a pressure within the fluid passageway, and wherein the second face is permanently located directly adjacent an atmospheric pressure outside the fluid passageway.

8. The regulator of claim 1, further comprising:
a venturi channel permanently located directly across the fluid passageway from the first face of the flexible member, wherein the venturi channel is configured to accelerate flow of fluid through an area adjacent the flexible member upon exposure to the differential pressure.

9. The regulator of claim 8, wherein the venturi channel is configured to cause an increased pressure drop in a flow path adjacent thereto in response to an increased pressure differential across the flexible member.

10. The regulator of claim 1, further comprising:
a thumb pad associated with the flexible member, wherein the thumb pad is configured to enable a user to override any automatic regulation of fluid flow, and to manually regulate flow of fluid through the fluid passageway.

11. A regulator for flow modulation during fluid collection, comprising:
a fluid transfer device comprising a tubular sidewall and a flexible member, wherein the flexible member is integrally formed within or secured to the tubular sidewall, wherein the tubular sidewall and the flexible member define a fluid passageway, wherein the flexible member is configured for movement with respect to the fluid passageway, wherein the flexible member comprises a first face directly adjacent an interior of the fluid passageway such that the first face is permanently located directly adjacent a first pressure in the fluid passageway, wherein the tubular sidewall defines an inner surface of the fluid passageway directly opposite the first face of the flexible member and directly adjacent the first pressure in the fluid passageway, wherein the flexible member comprises a second face opposite the first face, wherein the second face is located outside the fluid passageway such that the second face of the flexible member is permanently located directly adjacent a second pressure outside the fluid passageway resulting in the fluid passageway having a linear flow through architecture, wherein the flexible member is configured to at least partially collapse toward the inner surface of the fluid passageway to restrict a flow area of the fluid passageway upon exposure of the fluid transfer device to the differential pressure, wherein a contact member is provided on the first face of the flexible member, wherein the contact member extends from the first face of the flexible member toward the inner surface of the fluid passageway directly opposite the first face of the flexible member, and wherein, during an initial spike of vacuum pressure when the fluid transfer device is exposed to the differential pressure, the contact member abuts the inner surface of the fluid passageway to form a sealing point therewith to stop fluid flow through the fluid passageway.

12. The regulator of claim 11, wherein the flexible member includes a periphery surrounding the first face and the second face, wherein the periphery is integrally formed within or secured to the tubular sidewall.

* * * * *